United States Patent [19]

Jones

[11] 4,323,575

[45] Apr. 6, 1982

[54] 1-PHENYL-2-AMINOETHANOL DERIVATIVES

[75] Inventor: Geraint Jones, Macclesfield, England

[73] Assignee: Imperial Chemical Industries Limited, London, England

[21] Appl. No.: 147,074

[22] Filed: May 6, 1980

[30] Foreign Application Priority Data

May 21, 1979 [GB] United Kingdom ............... 17645/79

[51] Int. Cl.$^3$ ................. C07D 205/04; C07D 207/16; C07D 211/60; C07D 211/62; A61K 31/395; A61K 31/40; A61K 31/445

[52] U.S. Cl. ............................. 424/267; 260/239 A; 260/326.4; 546/226; 424/274

[58] Field of Search ...................... 546/226; 260/326.4, 260/239 A, 239 BF; 424/267, 274, 244

[56] References Cited

U.S. PATENT DOCUMENTS

| | | | |
|---|---|---|---|
| 3,607,859 | 9/1971 | Feder | 260/347.3 |
| 3,639,476 | 2/1972 | Eberle et al. | 260/563 |
| 3,933,911 | 1/1976 | Main | 260/562 N |
| 3,944,611 | 3/1976 | Smith | 260/562 R |
| 3,957,870 | 5/1976 | Main | 260/562 N |
| 4,041,075 | 8/1977 | Smith | 260/558 P |
| 4,211,878 | 7/1980 | Smith | 549/78 |

*Primary Examiner*—Norma S. Milestone
*Attorney, Agent, or Firm*—Cushman, Darby & Cushman

[57] ABSTRACT

The invention concerns compounds of the formula:-
$R^1$.CH(OH).CH$_2$NH.C$R^2R^3$.A$^1$. NH.CO.CH$R^4$.A$^2$.N$R^5$. Q I wherein $R^1$ is 3,4-bis[(3–8C)alkanoyloxy]-phenyl, 3,5- bis [(3–8C)alkanoyloxy]phenyl, 3-[(3–8C)alkanoyloxy]methyl-4-[(3–8C)alkanoyloxy]phenyl, 4-[(3–8C)alkanoyloxy]phenyl, 2-chlorophenyl or 3,5-dichloro-4-aminophenyl; $R^2$ and $R^3$ are independently hydrogen or (1–4C) alkyl; $A^1$ is (1–4C) alklylene; $A^2$ is a direct bond or (1–4C) alkylene; $R^4$ is hydrogen, (1–6C)alkyl, phenyl-(1–4C)alkyl or halogenophenyl-(1–4 C)alkyl; and $R^5$ is (1–6C)alkyl; or $R^4$ and $R^5$ together form (2–5C) alkylene; and Q is (3–12C) alkanoyl, [(3–6C)alkoxy]carbonyl, phenylacetyl, phenoxyacetyl, benzoyl or benzyloxycarbonyl, the phenyl rings of which may optionally bear a substituent selected from halogeno, (1–4C)alkyl, (1–4C)alkoxy and trifluoromethyl; and the pharmaceutically acceptable acid-addition salts thereof; processes for their manufacture; and pharmaceutical compositions thereof.

The compounds of formula I are topical anti-inflammatory agents. A representative compound is 1-[3,4-bis (pivaloyloxy)phenyl]-2-{2-[(N-phenylacetyl-proyly)amino]-1,1-dimethyl-ethylamino}ethanol.

9 Claims, No Drawings

1-PHENYL-2-AMINOETHANOL DERIVATIVES

This invention relates to 1-phenyl-2-aminoethanol derivatives which possess anti-inflammatory properties when applied topically to an area of inflammation; to pharmaceutical compositions thereof; and to processes for the manufacture thereof.

It is known from our earlier work that certain 1-phenoxy-3-aminopropan-2-ol derivatives bearing an [(N-acyl)aminoalkanoyl]aminoalkyl substitutent on the 3-amino radical possess $\beta$-adrenergic blocking properties (UK Pat. Ser. No. 1,540,463). It is also known from other of our earlier work that certain esters of dihydroxyphenylethanolamine derivatives possess anti-inflammatory properties when applied topically to an area of inflammation, that is they possess topical anti-inflammatory properties (West German Offenlegungsschrift No. 2,756,001).

We have now discovered, and herein lies our invention, that certain new 1-phenyl-2-aminoethanol derivatives bearing on the 2-amino radical an [(N-acyl)aminoalkanoyl]aminoalkyl substitutent in which the amino moiety of the aminoalkanoyl radical is secondary, surprisingly possess topical anti-inflammatory properties.

Accordingly, the invention provides a 1-phenyl-2-aminoethanol derivative of the formula:

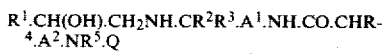

wherein $R^1$ is selected from 3,4-bis[(3–8C)alkanoyloxy]phenyl, 3,5-bis[(3–8C)alkanoyloxy]phenyl, 3-[(3–8C)alkanoyloxy]methyl-4-[(3–8C)alkanoyloxy]phenyl, 4-[(3–8C)alkanoyloxy]phenyl, 2-chlorophenyl and 3,5-dichloro-4-aminophenyl radicals; $R^2$ and $R^3$ are independently selected from hydrogen and (1–4C)alkyl radicals; $A^1$ is a (1–4C)alkylene diradical; $A^2$ is selected from a direct bond and a (1–4C)alkylene diradical; $R^4$ is selected from hydrogen, (1–6C)alkyl, phenyl-(1–4C)alkyl and halogenophenyl-(1–4C)alkyl radicals; and $R^5$ is a (1–6C)alkyl radical; or $R^4$ and $R^5$ together form a (2–5C)alkylene diradical; and Q is selected from (3–12C)alkanoyl, [(3–6C)alkoxy]carbonyl, phenylacetyl, phenoxyacetyl, benzoyl and benzyloxycarbonyl radicals, the phenyl rings of which may optionally bear a substituent selected from halogeno, (1–4C)alkyl, (1–4C)alkoxy and trifluoromethyl radicals; or a pharmaceutically acceptable acid-addition salt thereof.

It will be observed that a compound of formula I possesses at least one asymmetric carbon atom, that is the carbon atom bearing $R^1$, and depending on the nature of its substitutents, also additional asymmetric carbon atoms, and can therefore exist in racemic and optically-active forms. This invention relates to the racemic form(s) of a compound of formula I and to any optically-active form which possesses anti-inflammatory activity, is being well known in the art how to prepare optically active forms by resolution of a racemic form, or by synthesis from optically active starting materials, and how to determime the topical antiinflammatory activity by the standard tests described hereinbelow.

A particular value for a (3–8C)alkanoyloxy radical present on $R^1$ is, for example, a 2,2-dimethylpropionyloxy (pivaloyloxy), isobutyryloxy, n-butyryloxy, n-pentanoyloxy (valeryloxy), or 3,3-dimethylbutryloxy radical, of which values a 2,2-dimethylpropionyloxy is preferred.

Specific values for $R^1$ which are of special interest are, for example, a 3,4-bis(pivaloyloxy)phenyl, 3,5-bis(pivaloyloxy)phenyl, 3,4-bis(butyryloxy)phenyl, 3-(isobutyryloxymethyl)-4-(isobutyryloxy)phenyl, 4-(pivaloyloxy)phenyl, 2-chlorophenyl and 3,5-dichloro-4-aminophenyl radicals.

A particular value for $R^2$ or $R^3$ when it is a (1–4C)alkyl radical is, for example, a methyl radical.

A preferred value for $R^2$ and $R^3$ is, for example, when they are both hydrogen or methyl radicals, of which the latter value is especially preferred.

A particular value for $A^1$ is, for example, a methylene or ethylene diradical, of which a methylene diradical is preferred.

A particular value for $A^2$ when it is a (1–4C)alkylene radical is, for example, a methylene or ethylene diradical.

A preferred value for $A^2$ is when it is a direct bond, or a methylene or ethylene diradical.

A particular value for $R^4$ when it is a (1–6C)alkyl radical is, for example, a methyl, ethyl, propyl, isopropyl, butyl, isobutyl or sec-butyl; and when it is a phenyl-(1–4C) is, for example, a benzyl or phenylethyl; and when it is a halogenophenyl(1–4C)alkyl is, for example, a chlorobenzyl or (chloropenyl)ethyl radical.

A particular value for $R^5$ is, for example, a methyl, ethyl, propyl or butyl radical.

A particular value for $R^4$ and $R^5$ when together they form a (2–5C)alkylene diradical is, for example, an ethylene, trimethylene or tetramethylene diradical.

A particular value for Q when it is a (3–12C)alkanoyl radical is, for example, an isobutyryl or dodecanoyl radical; and when it is a [(3–6C)alkoxy]carbonyl radical is, for example, a t-butoxycarbonyl radical.

Particular values for phenyl ring substituents which may be present as part of Q are for example: for a halogeno radical, a fluoro, chloro or bromo radical; for a (1–4C)alkyl radical, a methyl radical; and for a (1–4C-)alkoxy radical, a methoxy radical.

Specific values for Q which are of particular interest are, for example, when it is a t-butoxycarbonyl, benzyloxycarbonyl, phenylacetyl, phenoxyacetyl, benzoyl, 4-chlorophenylacetyl or 4-chlorobenzoyl radical.

A particular group of compounds of the invention which is of special interest comprises compounds of the formula:

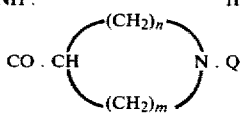

wherein $R^1$, $R^2$, $R^3$, $A^1$ and Q have any of the general or specific meanings defined above, n is zero, 1 or 2, and m is 2, 3, 4 or 5; together with the pharmaceutically acceptable acid-addition salts thereof.

Still further groups of compounds of the invention which are of special interest are comprised by those compounds of formula II wherein $R^1$, $R^2$, $R^3$, $A^1$ and Q have any of the general or specific meanings defined above and n and m have any one of the following combinations of values:

(i) $n=0$, $m=2$
(ii) $n=0$, $m=3$ (iii) n=0, m=4
(iv) n=1, m=2
(v) n=1, m=3
(vi) n=2, m=2 together with the pharmaceutically acceptable acidaddition salts thereof.

A particular value for the diradical of the formula:

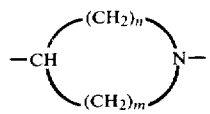

is, for example, azetidin-1,2-diyl pyrrolidin-1,2- or 1,3-diyl, piperidin-1,2-, -1,3- or -1,4-diyl radical, of which an azetidin-1,2-diyl, pyrrolidin-1,2-diyl or piperidin-1,2-diyl radical is especially preferred.

A particular acid-addition salt of a compound of formula I or II is, for example, a salt derived from an acid having a pharmaceutically acceptable anion, for exampl from an inorganic acid, for example hydrochloric, hydrobromic, phosphoric or sulphuric acid, or from an organic acid, for example oxalic, tartaric, lactic, fumaric citric, acetic, salicylic, benzoic, β-naphthoic, methanesulphonic or adipic acid.

Specific compounds of the invention are described in the accompanying Examples, but of these the following compounds are of special interest:

1-[3,4-bis(pivaloyloxy)phenyl]-2-{2-[(N-phenylacetyl-propyl)amino]-1,1-dimethyl-ethylamino}ethanol; 1-(2-chlorophenyl)-2-{2-[(N-benzoyl-piperidin-2-carbonyl)amino]-1,1-dimethyl-ethylamino}ethanol; 1-[3,5-bis(pivaloyloxy)phenyl]-2-{2-[(N-phenoxyacetyl-propyl)amino]-1,1-dimethyl-ethylamino}ethanol; 1-[3,4-bis(pivaloyloxy)phenyl]-2-{2-[(N-phenoxyacetyl-N-methylglycyl)amino]-1,1-dimethyl-ethylamino}ethanol; 1-[3,4-bis(pivaloyloxy)phenyl]-2-{2-[N-phenoxyacetyl-N-methyl-γ-alanyl]amino]-1,1-dimethyl-ethylamino}-ethanol; and their pharmaceutically acceptable acid-addition salts.

The compounds of the invention may be manufactured by any chemical process known to be useful for the manufacture of chemically analogous compounds, for example those processes described in UK Pat. specification Ser. No. 1,540,463 or West German Offenlegungsschrift No. 2,756,001. Such processes are provided as a feature of the invention and are illustrated by the following preferred processes wherein $R^1$, $R^2$, $R^3$, $R^4$, $R^5$, $A^1$, $A^2$ and Q have any of the meanings defined hereinbefore.

(a) A glyoxal of the formula:

$$R^1CO.CHO \qquad \qquad IV$$

or a hydrate thereof, is reacted with an amino compound of the formula:

$$H_2N.CR^2R^3.A^1.NH.CO.CHR^4.A^2.NR^5.Q \qquad V$$

under reducing conditions.

Particular suitable reducing conditions are provided by using, for example, an alkali metal borohydride or cyanoborohydride, for example sodium borohydride or cyanoborohydride, conveniently in an inert solvent or diluent, for example acetonitrile, methanol, ethanol or 2-propanol and at a temperature in the range, for example −20° C. to 30° C. When sodium cyanoborohydride is used, which is preferred, the reaction is preferably carried out at or near pH 4, for example in the presence of acetic acid. Other standard reducing conditions may be suitable provided they are compatible with the substituents present in the starting material.

It will be appreciated that processes of the above general type are known as reductive alkylations, and proceed at least in part through an intermediate of the formula:

$$R^1.U.CH=N.CR^2R^3.A^1.NH.CO.CHR^4.A^2.NR^5.Q \qquad VI$$

wherein U is a hydroxymethylene diradical and/or of the formula VI wherein U is a carbonyl diradical. Such an intermediate of formula VI wherein U is a hydroxymethylene or a carbonyl diradical (or a mixture thereof) may be prepared and then reduced in two separate stages in process (a) if desired.

The glyoxals of formula IV may be obtained, for example, by selenium dioxide oxidation of an acetophenone of the formula:

$$R^1CO.CH_3 \qquad \qquad VII$$

in an appropriate solvent, for example aqueous dioxan, at a temperature in the range, for example, 50°–150° C., optionally followed by hydrate formation.

Alternatively, the glyoxals of formula IV may be conveniently obtained by dimethyl sulphoxide oxidation of the appropriate phenacyl bromide derived by bromination of the corresponding acetophenone of formula VII, for example as illustrated in the Examples hereinafter.

The amino compounds of formula V may be obtained by reaction of an acid of the formula:

$$HO_2C.CHR^4.A^2.NR^5.Q \qquad VIII$$

with a diamine of the formula:

$$H_2N.CR^2R^3.A^1.NH_2 \qquad IX$$

The acid of formula VIII is preferably first converted to a reactive derivative, such as its mixed anhydride with a (1-4C)alkyl acid carbonate, obtainable by reacting the acid of formula VIII with a [(1-4C)alkoxy]carbonyl chloride in the presence of a tertiary base such as N-methylmorpholine. This procedure is illustrated in the accompanying Examples and enables the amino compounds of formula V to be prepared at a temperature at or below room temperature, thus resulting in the minimum of racemisation when an optically active acid of formula VIII is used ($R^4$ is other than hydrogen).

The acids of formula VIII may themselves be obtained by acylation of the appropriate amino acid of the formula:

$$HO_2C.CHR^4.A^2.NR^5.H \qquad X$$

with an acylating agent derived structurally from an acid of the formula Q.OH, for example a chloride or bromide of such an acid, using conventional mild reaction conditions which minimise racemisation of optically active amino acids of formula X, for example as illustrated in the accompanying Examples.

The amino acids of formula X and the diamines of the formula IX may be obtained by standard methods well known in the art of organic chemistry.

(b) A compound of the formula:

$$R^1.CO.CH_2.NH.CR^2R^3.A^1.NH.CO.CHR^4.A^2.NR^5.Q \quad XI$$

is reduced.

The reduction may be carried out using any agent generally known for reducing aromatic ketones, but which is compatible with the other substituents present in the starting material of formula XI. Thus the reduction may be carried out by means of an alkali metal borohydride, for example sodium borohydride or cyanoborohydride, in an appropriate diluent or solvent, for example methanol, ethanol or 2-propanol. [These conditions are particularly suitable when $R^1$ is a 2-chlorophenyl or 3,5-dichloro-4-aminophenyl radical.] The reduction may also be carried out by means of catalytic hydrogenation, for example with hydrogen in the presence of a palladium, platinum or nickel, catalyst and preferably under a pressure of hydrogen of, for example, up to 5 bars, in a diluent or solvent, for example, ethanol or acetic acid. [These conditions are particularly suitable when $R^1$ is other than a 2-chlorophenyl or 3,5-dichloro-4-aminophenyl radical.] In either case the reduction is generally performed at a temperature of, for example $-20°$ C. to $50°$ C. and conveniently at or near normal room temperature, for example at $15°$ to $30°$ C.

The starting materials of formula XI may be obtained by reacting a phenacyl halide of the formula:

$$R^1.CO.CH_2.Hal \quad XII$$

wherein Hal. is a chloro or bromo radical, with an amino compound of the formula V.

This reaction is conveniently carried out at or near normal room temperature, for example from $15°$ to $30°$ C., and in a diluent or solvent, for example ethanol, dioxan, chloroform or acetonitrile. It may also be carried out in the presence of an acid-binding agent, for example pyridine, triethylamine or an alkali metal carbonate or bicarbonate, or an excess of the amino compound of formula V.

The phenacyl halides of formula XII may be obtained by conventional procedures of organic chemistry.

(c) A compound of the formula:

$$R^1.U.CH_2N.CR^2R^3.A^1.NH.CO.CHR^4.A^2.NR^5.Q \quad XIII$$
$$\underset{W}{|}$$

wherein U is a carbonyl or hydroxymethylene diradical and W is a benzyl or substituted benzyl radical is hydrogenolysed.

This process is not applicable to the production of compounds of the invention wherein Q is a benzyloxycarbonyl radical.

A particular value for W when it is a substituted benzyl radical is, for example, a 4-methylbenzyl radical.

The hydrogenolysis must necessarily be carried out under conditions which do not affect substituents present on $R^1$, and is therefore preferably carried out by means of catalytic hydrogenation, for example with hydrogen in the presence of a palladium, platinum or nickel catalyst in a suitable diluent or solvent, for example 2-propanol, ethanol or water, or a mixture thereof, conveniently at a temperature in the range, for example, $15°$-$30°$ C. and optionally under a pressure of up to 5 bars.

It will be appreciated that when U is a carbonyl diradical in the starting material of formula XIII it is necessary to carry out the hydrogenolysis under greater than atmospheric pressure of hydrogen so that concomitant reduction of the carbonyl diradical also takes place.

Those starting materials of formula XIII wherein U is a hydroxymethylene diradical may be obtained, for example, by sodium borohydride reduction of the corresponding ketone of the formula:

$$R^1.CO.CH_2.N.CR^2R^3.A^1.NH.CO.CHR^4.A^2.NR^5.Q \quad XIV$$
$$\underset{W}{|}$$

wherein W has the meanings defined above, using similar solvents and temperature to those described earlier for process (a). Such starting materials are conveniently prepared and used in situ in process (c).

The ketones of formula XIV (which are also starting materials of formula XIII wherein U is a carbonyl diradical) may themselves be prepared by reaction of the appropriate phenacyl halide of formula XII with an amino compound of the formula:

$$W.NH.CR^2R^3.A^1.NH.CO.CHR^4.A^2.NR^5.Q \quad XV$$

wherein W has the meanings defined above, using analogous reaction conditions to those described in connection with process (b) for the production of starting material of formula XI.

The amino compounds of formula XV may be conveniently obtained by reductive alkylation of the appropriate amino compound of formula V using the appropriate benzaldehyde and a reducing agent such as sodium cyanoborohydride, and employing similar conditions to those specified hereinbefore for process (a).

Process (c) is particularly useful for the production of those compounds of the invention wherein $R^1$ is other than a 2-chlorophenyl or 3,5-dichloro-4-aminophenyl radical, and $R^2$ and $R^3$ are both hydrogen. It is preferably performed using starting materials of formula XIII wherein U is a hydroxymethylene diradical.

A compound of formula I in free base form may be converted into a pharmaceutically acceptable acid-addition salt by reaction with a suitable acid, as defined hereinbefore, using conventional means which avoid hydrolysis of any ester groups. Alternatively, when a hydrogen chloride or bromide salt is required, this may be conveniently obtained by producing a stoichiometric amount of the hydrogen halide in situ by catalytic hydrogenation of the appropriate benzyl halide, preferably in an inert solvent or diluent, for example, ethanol and at, or near, room temperature.

The compounds of formula I may conveniently be used as their pharmaceutically acceptable acid-addition salts.

Optically-active forms of a compound of formula I may be obtained by conventional resolution of the corresponding racemic form of a compound of formula I. Thus, a racemic form of a compound of formula I may be reacted with an optically-active acid, followed by fractional crystallisation of the diastereoisomeric mixture of salts thus obtained from a suitable solvent, for example ethanol, whereafter the optically-active form of a compound of formula I may be liberated by treatment under conditions which avoid loss of any sensitive functional groups (such as esters) which may be present, for example by using anion exchange chromatography.

A particularly suitable optically-active acid is, for example (+)- or (−)-O,O-di-p-toluoyl-tartaric acid, or (−)-2,3:4,5-di-O-isopropylidene-2-keto-L-gulonic acid.

In addition, compounds of formula I having at least some of their asymmetrically substituted carbon atoms with a specific optical configuration may also be obtained by incorporating optically active starting materials, such as optically active α-amino acids, in the above synthetic processes.

As stated above, the compounds of formula I possess anti-inflammatory activity when applied topically to an area of inflammation and, in particular, are therefore useful in treating inflammatory diseases or inflammatory conditions of the skin, in warm-blooded animals.

The anti-inflammatory properties of a compound of formula I may be demonstrated in a standard test involving the inhibition of croton oil induced inflammation on the mouse ear. The activity of an individual compound of formula I in this test depends upon its particular chemical structure, but in general compounds of formula I produce a significant inhibition of the inflammation at a topically applied dose of 0.30 mg. per ear or much less.

Another standard test in which the antiinflammatory properties of a compound of formula I may be demonstrated involves the inhibition of oxazolone induced contact sensitivity on the mouse ear. In general, compounds of formula I produce significant inhibition of the inflammation in this test at a topically applied dose of 2.5 mg. per ear, or much less.

No overt toxic effects are detected at the active doses in either of the above tests, with the compounds of formula I described herein.

In general, a compound of formula I may be used in the treatment of inflammatory diseases or inflammatory conditions of the skin in an analogous manner to that in which known topically active antiinflammatory agents, for example, the topically active steroids, are used.

When used for the topical treatment of an area of inflammation affecting the skin of a warm-blooded animal, for example man, a compound of formula I may be administered topically at a dose in the range 10 μg. to 10 mg./cm$^2$, or at an equivalent dose of a pharmaceutically acceptable acid-addition salt thereof, and, if necessary, a dose in this range is repeated at intervals of, for example, 4–12 hours. However, it will be appreciated that the total daily amount of a compound of formula I administered necessarily depends on the extent and severity of the inflammation under treatment.

The compounds of formula I may be administered in the form of pharmaceutical compositions and according to a further feature of the invention there is provided a pharmaceutical composition comprising a compound of formula I, or a pharmaceutically acceptable acid-addition salt thereof, in association with a pharmaceutically acceptable excipient in a form suitable for topical administration, for example in the form of an ointment, gel, aqueous or oily solution or suspension, emulsion or aerosol formulation. A pharmaceutical composition according to this aspect of the invention may contain from 0.1% to 5% w/w of a compound of formula I, or an equivalent amount of a pharmaceutically acceptable acid-addition salt thereof, hereinafter referred to as an active ingredient.

The pharmaceutical compositions may be made by methods well known in the art for the production of topical formulations, using conventional pharmaceutically acceptable excipients.

Thus, a particular ointment formulation may be prepared by dispersing an active ingredient as defined above in a suitable organic diluent, for example soft paraffin, optionally in the presence of an emulsifying and/or thickening agent, for example sorbitan monostearate.

A particular gel formulation may be prepared by adding a gelling agent, for example carboxy-polymethylene, to a solution of an active ingredient as defined above in a suitable organic solvent, for example isopropyl alcohol.

A particular emulsion formulation, for example a cream or a lotion, may be prepared by mixing an active ingredient as defined above with a suitable conventional emulsifying system and water.

The pharmaceutical compositions may also conveniently contain one or more other conventional excipients, for example a solubilising agent such as polyethylene glycol, propylene glycol, diethylene glycol monomethyl or monoethyl ether, or benzyl alcohol; and/or a penetration enhancer such as dimethyl sulphoxide, N-methylpyrrolidin-2-one, or pyrrolidin-2-one, and/or conventional stabilising agents and antioxidants, in order to produce a stable topical formulation which results in significant absorption of the active ingredient into the skin.

A pharmaceutical composition according to this aspect of the invention may contain in addition to an active ingredient as defined above, at least one known pharmaceutical agent selected from: corticosteroids, for example fluocinolone acetonide, prednisolone, flumethasone pivalate, betamethasone valerate, hydrocortisone or dexamethasone; phosphodiesterase inhibitors, for example theophylline or caffeine; antibacterial agents, for example oxytetracycline, gentamicin, neomycin, gramicidin, chlorhexidine or cetyltrimethylammonium bromide; anti-fungal agents, for example griseofulvin or nystatin; antihistamines, for example diphenhydramine or chlorphenamine; local anaesthetics, for example amylocaine, benzocaine or procaine; and emollients, for example calomine.

In addition the compositions of the invention may also contain conventional excipients, such as colours, chelating agents, dispersing agents or preservatives, as desired.

The invention is illustrated, but not limited, by the following Examples in which:

(i) unless otherwise stated, all procedures were carried out at room temperature (in the range 18°–26° C.) and at atmospheric pressure;

(ii) all evaporations were performed by rotary evaporation under reduced pressure;

(iii) nuclear magnetic resonance (NMR) data, where given, is given in the form of chemical shifts (δ values) for characteristic protons, relative to tetramethyl silane (TMS) as standard, determined in d$_6$DMSO as solvent (unless stated otherwise) and at 100 MH$_z$;

(iv) the compounds of formula I in general had satisfactory microanalyses but in cases of doubt characteristic NMR spectral data is given;

(v) melting points given are those actually obtained and are intended to serve as a guide when repeating the Examples and are not necessarily the absolute values for fully crystalline compounds; and (vi) yields, where given, are purely illustrative and are not to be construed as the maximum attainable.

EXAMPLES 1–4

A solution of 3,4-bis(pivaloyloxy)phenylglyoxal (1.67 g.) and $N^1$-(2-amino-2-methylpropyl)-$N^2$-phenylacetyl-prolinamide (1.51 g.) in acetic acid (4 ml.) and acetonitrile (20 ml.) was stirred for 10 minutes and then treated with sodium cyanoborohydrie (0.63 g.) and this mixture stirred for 3.5 hours. Water (20 ml.) was then added and the subsequent mixture was extracted with ethyl actate ($3\times75$ ml.). The combined extracts were washed with saturated sodium chloride solution, dried (MgSO$_4$), and evaporated. The residue (3.48 g.) was purified by chromatography on silica gel (80 g., particle size 0.04–0.63 mm) using a mixture containing 1 part by volume of methanol in 49 parts by volume of chloroform as eluant. The fractions containing the major basic component were collected and evaporated. The residue was dissolved in chloroform (10 ml.) and the solution acidified with ethanol hydrogen bromide. The solvent was evaporated and any excess hydrogen bromide was eliminated by repeated solution in chloroform followed by evaporation. There was thus obtained 1-[3,4-bis(pivaloyloxy)phenyl]-2-{-2-[(N-phenylacetyl-prolyl)amino]-1,1-dimethyl-ethylamino}ethanol hydrobromide (Example 1) as a foam (0.35 g.); microanalysis, found: N, 6.0%; $C_{35}H_{49}N_3O_7$.HBr requires N, 6.0%; NMR $\delta$: 8.8–7.9 (3H, broad, NHCO+N$^+$H$_2$); 7.5–7.0 (8H, complex, aromatic H); 5.04 (1H, broad, C$\underline{H}$OH); 3.7–2.7 (6H, complex, CH$_2$N) 3.75 (singlet, PhC$\underline{H}_2$); 2.2–1.8 (4H, complex, —C$\underline{H}_2$—C$\underline{H}_2$—) 1.27 (24H, singlet, CH$_3$).

Using an analogous procedure, but starting from the appropriate glyoxal of formula IV and amino compound of formula V, the following compounds of formula I were obtained:

(Example 2): 1-[3,4-bis(pivaloyloxy)phenyl]-2-{2-[(N-phenoxyacetyl-proly)amino]-1,1-dimethyl-ethylamino}ethanol hydrobromide, as a foam (20% yield), m.p.~116° C.; microanalysis, found: C, 54.0; H, 6.7; N, 5.5%; calculated for $C_{35}H_{49}N_3O_8$.HBr.3H$_2$O: C, 54.3; H, 7.1; N, 5.4%; (Example 3): 1-(3-isobutyryloxymethylene-4-isobutyryloxyphenyl)-2-{2-[(N-phenylacetyl-propyl)amino]-1,1-dimethyl-ethylamino}ethanol hydrobromide, as a foam (12% yield); NMR ($\delta$): 8.6–8.0 (4H, broad, NHCO+N$^+$H$_2$); 7.6–6.6 (8H, complex, aromatic H), 4.95+4.90 (3H: singlet, i-Pr.CO$_2$C$\underline{H}_2$; broad, C$\underline{H}$OH); 4.4–2.6 [complex; H$_2$O+CH$_2$N+(CH$_3$)$_2$C$\underline{H}$+=N—CH—CO]; 3.65 (singlet, PhC$\underline{H}_2$CO); 2.0–1.8 (4H, complex, =NCH$_2$C$\underline{H}_2$C$\underline{H}_2$); 1.1 [18H, quartet, (C$\underline{H}_3$)$_2$CH+C(CH$_3$)$_2$];

(Example 4): 1-(3,5-dichloro-4-aminophenyl)-2-{2-[(N-phenoxyacetyl-prolyl)amino]-1,1-dimethyl-ethylamino}ethanol hydrobromide as a solid (11% yield), m.p. 123°–128° C.; NMR ($\delta$): 9.0–8.0 (3H, complex, NHCO+N$^+$H$_2$); 7.5–6.7 (7H, complex, aromatic H); 6.1 (broad, NH$_2$+H$_2$O); 4.8–4.5 (3H: singlet, PhOC$\underline{H}_2$CO; multiplet, C$\underline{H}$OH); 4.3 (1H, complex, =N—CH—CO); 3.8–2.8 (6H, complex, NC$\underline{H}_2$); 2.2–1.6 (4H, complex, NCH$_2$C$\underline{H}_2$C$\underline{H}_2$); and 1.22 (6H, singlet CH$_3$).

The necessary starting materials of formula V were obtained as follows:

A solution of L-proline (23 g., 0.2 mole) in 2 N sodium hydroxide (120 ml.) was cooled at 0°–5° C. and treated with a total of phenylacetyl chloride (34.0 g., 0.22 mole) and 2 N sodium hydroxide (120 ml.) in ten equal and alternate portions with vigorous intermittent shaking and ice-cooling. The mixture was maintained at an alkaline pH by the addition of extra 2 N sodium hydroxide as necessary. After the addition of the reagents was complete, the mixture was shaken for 15 minutes to give a clear solution, which was acidified to pH~2 with ice-cooling by dropwise addition of concentrated hydrochloric acid. The acidic solution was cooled to give N-phenylacetylproline as a solid (46.4 g.) (m.p. 135°–6° C. after recrystallisation from methanol)

N-Phenoxyacetyl-proline was obtained in a similar manner as a solid, m.p. 109°–11° C.

A mixture of N-phenylacetyl-proline (17.4 g.), N-methylmorpholine (7.85 ml.) and analytical grade chloroform (60 ml.) was stirred at room-temperature for 5 minutes. After cooling to −23° C., isobutyl chloroformate (9.23 ml.) was added rapidly during 1 minute. An exothermic reaction occurred and the temperature rose to −15° C. After a further 1 minute of stirring, 1,2-diamino-2-methylpropane (7.86 ml.) was added rapidly and the temperature was allowed to rise to room-temperature with stirring during 2 hours. The mixture was then poured into water (50 ml.) and the organic layer separated and discarded. The aqueous layer was basified (solid potassium carbonate) and extracted with chloroform ($4\times100$ ml.). The chloroform extracts were dried (MgSO$_4$) and evaporated under high vacuum to give $N^1$-(2-amino-2-methylpropyl)-$N^2$-phenylacetyl-prolinamide as an oil (15.5 g.); NMR ($\delta$) (CDCl$_3$): 7.7–6.7 (6H, complex, aromatic H+NHCO); 4.5 (1H, complex, =N—CH—CO); 3.8–2.7 (6H, complex CH$_2$N+PhC$\underline{H}_2$); 3.65 (singlet, PhC$\underline{H}_2$); 2.4–1.6 (6H, complex, C$\underline{H}_2$C$\underline{H}_2$CH+NH$_2$); and 1.0 [6H, singlet, C(C$\underline{H}_3$)$_2$].

Using a similar procedure, but starting with N-phenoxyacetyl-proline, $N^1$-(2-amino-2-methylpropyl)-$N^2$-phenoxyacetyl-prolinamide was obtained as an oil, NMR ($\delta$): 7.7–6.7 (6H, complex, NHCO+aromatic H); 4.6 (3H, complex, PhOC$\underline{H}_2$CO+=N—CH—CO); 3.8–2.7 (4H, complex, CH$_2$N); 2.5–1.5 (6H, complex, NCH$_2$C$\underline{H}_2$CH$_2$+NH$_2$); 1.0 [6H, singlet, C(CH$_3$)$_2$].

The glyoxal starting materials of formula IV were obtained as follows:

(1) 3,4-Bis(pivaloyloxy)phenylglyoxal:

A suspension of 3,4-dihydroxy-acetophenone (13.1 g., 0.08 mole) in chloroform (320 ml.) was cooled in an ice bath to 0°–5° C. A solution of pivaloyl chloride (19.2 ml., 0.16 mole) in chloroform (80 ml.) and a solution of triethylamine (22.2 ml., 0.16 mole) in chloroform (80 ml.) were added dropwise simultaneously to the stirred suspension during 10 minutes. The reaction mixture was stirred at 0°–5° C. for a further 1 hour and then was poured into a mixture of 2 N-hydrochloric acid (100 ml.) and ice (200 g.). The mixture was extracted with chloroform ($3\times150$ ml.), and the extracts washed successively with water (100 ml.), 10% w/v sodium carbonate solution (100 ml.), water (100 ml.) and brine (100 ml.). After drying (MgSO$_4$) the combined extracts were evaporated to give crude 3,4-bis(pivaloyloxy)acetophenone as an oil (23.1 g.) which was used without purification.

A solution of bromine (3.15 ml., 0.061 mole) in chloroform (50 ml.) was added dropwise at room temperature to a stirred solution of 3,4-bis(pivaloyloxy)acetophenone (19.5 g., 0.061 mole) and t-butyl acetate (8.2 ml., 0.06 mole) in chloroform (150 ml.) containing a catalytic amount of anhydrous aluminium chloride (0.2 g.). The reaction mixture was stirred at room temperature for 1 hour after the addition was complete, chromatographic silica gel (75 g.) was then added and the mixture evaporated in vacuo. The residual solid was added to the top of a column of dry chromatographic silica-gel (1 kg., previously deactivated by addition of 10% w/w water and then equilibrated with 10% v/w of a 5% v/v solution of ethyl acetate in toluene). The column was developed by elution with a 5% v/v solution (1100 ml.) of ethyl acetate in toluene. The column was then eluted with ethyl acetate (2×500 ml.) and the fractions collected were monitored by thin layer chromatography (TLC) (on silica plates developed in a 50% v/v mixture of ethyl acetate and toluene). The later fractions were combined and evaporated to give 2-bromo-3,4-bis(pivaloyloxy)-acetophenone as an oil (14.2 g.) which rapidly crystallised to give a solid of m.p. 64°-66° C.

A solution of 2-bromo-3,4-bis(pivaloyloxy)acetophenone (2 g.) in dimethyl sulphoxide (10 ml.) was allowed to stand for 18 hours at room-temperature, then poured into ice-water and extracted with ether (3×50 ml.).

The ether extracts were washed with water (50 ml.) and brine (50 ml.), dried (MgSO$_4$) and evaporated to give 3,4-bis(pivaloyloxy)phenylglyoxal as an oil (1.8 g.); infra-red$\nu$max.: 1760 cm$^{-1}$ (ester >C=O), 1690 cm$^{-1}$ (—CO.CHO); δ(CDCl$_3$): 8.2—7.1 (complex, aromatic —H), 1-35 (18H, singlet —C.CH$_3$).

(2) 3-Isobutyryloxymethyl-4-isobutyryloxyphenylglyoxal:

This compound was prepared as an oil having a satisfactory infra-red (IR) absorption spectrum by oxidation of the corresponding α-bromoacetophenone with dimethylsulphoxide. The α-bromoacetophenone was itself obtained as follows:

Sodium hydride (2.0 g.) was added in portions to stirred isobutyric acid (150 ml.) over a period of 15 minutes. 3-Acetoxymethyl-4-acetoxy-acetophenone (40 g.) was then added, and the mixture was heated to 160° C. and maintained at this temperature with stirring for 15 hours. The mixture was then concentrated by distilling under reduced pressure while maintaining the temperature at 160° C. The gummy residue was cooled and dissolved in ether (500 ml.). This solution was washed with 10% w/v sodium carbonate solution (3×250 ml.), water (2×500 ml.) and saturated brine (250 ml.). The organic phase was dried (MgSO$_4$), filtered and evaporated to give a brown oil. This was distilled under high vacuum to give 3-isobutyryloxymethyl-4-isobutyryloxyacetophenone as a colourless viscous liquid; NMR (δ) (CDCl$_3$): 8.2-7.1 (3H, 1,2,4-aromatic H pattern); 5.1 (2H, singlet CO$_2$CH$_2$); 2.55+2.67 (5H, singlet, COCH$_3$. +doublet, CHCO$_2$); 1.21+1.15 [12H, 2 doublets (J 8.3 c/s), (CH$_3$)$_2$CH].

A solution of 3-isobutyryloxymethyl-4-isobutyryloxy-acetophenone (8.8 g.) in dimethylsulphoxide (35 ml.) was left at room temperature for 2 days and then poured into an excess of ice-water. The mixture was extracted with ethyl acetate (3×100 ml.). The extracts were washed successively with saturated sodium bicarbonate solution (50 ml.), water (3×50 ml.) and saturated sodium chloride solution (50 ml.), and then evaporated to yield 3-isobutyryloxymethyl-4-isobutyryloxy-α-bromoacetophenone as an oil having a satisfactory IR spectrum and pure by thin layer chromatography (TLC) [SiO$_2$: 50 % v/v EtOAc/petrol (b.p. 60°-80° C.)].

(3) 4-amino-3,5-dichlorophenylglyoxal:

This compound was obtained as a solid hydrate, m.p. 95°-98° C., in 58% yield by oxidation of 4-amino-3,5-dichloroacetophenone (12.0 g.) with selenium dioxide (10.0 g.) in a mixture of dioxan (60 ml.) and water (2 ml.), at 95° C. for four hours, followed by evaporation of the filtered mixture.

EXAMPLES 5-28

Using an analogous procedure to that described in Example 1 but starting from the appropriate glyoxal of formula IV and amino compound of formula V, the following compounds of formula I were obtained:

(Example 5): 1-[3,5-bis(pivaloyloxy)phenyl]-2-{2-[(N-phenylacetyl-prolyl)amino]-1,1-dimethyl-ethylamino}ethanol hydrobromide as a solid (13% yield), m.p. 150°-156° C. (decomposition); NMR (δ): 8.7—8.0 (3H, complex, NHCO+N$^+$H$_2$); 7.4-6.6 (8H, complex, aromatic H); 4.9 [1H, doublet (J=8 c/s), CHOH], 4.3 (multiplet,

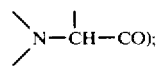

4.0—2.7 (complex, CH$_2$N+H$_2$O); 2.2—1.7 (4H, complex, >NCH$_2$CH$_2$CH$_2$); 1.3 (24H, complex, CH$_3$C);

(Example 6): 1-(2-chlorophenyl)-2-{2-[(N-benzoyl-piperidin-2-carbonyl)amino]-1,1-dimethyl-ethylamino}ethanol hydrobromide as a foam (25% yield), m.p.~102° C.; NMR (δ): 8.3—8.6 (3H, complex, OH+N$^+$H$_2$); 8.2 (triplet, NHCO); 8.0—7.2 (9H, complex, aromatic H); 5.34 [1H, doublet (J=9 1 c/s), CHOH); 4.2 (1H, complex, >N—CH—CO); 3.7—2.7 (complex, CH$_2$N); 1.8—1.0+1.3 (12H, complex+singlet. >NCH$_2$CH$_2$CH$_2$CH$_2$+CH$_3$C];

(Example 7): 1-(3,4-bis(pivaloyloxy)phenyl]-2-{2-[(N-benzoylopropyl)amino]-1,1-dimethyl-ethylamino}ethanol hydrobromide as a solid (8% yield), m.p. 175°-179° C.; NMR (δ): 9.2—7.8 (4H, complex, NHCO+N$^+$H$_2$+OH); 7.8-6.8 (8H, complex, aromatic H); 5.24 [2H, doublet (J=8 c/s), CHOH]; 4.68 (1H, complex, >N—CH—CO); 4.0-2.7 (6H, complex, CH$_2$N); 2.7—1.7 (4H, complex, >N—CH$_2$CH$_2$CH$_2$); 1.5+1.36 (24H, doublet+singlet, CH$_3$C);

(Example 8): 1-(2-chlorophenyl)-2-{2-[(N-benzoylprolyl)amino]-1,1-dimethyl-ethylamino}ethanol hydrobromide as a foam (30% yield), m.p.~89° C., NMR (δ): 9.2—8.2 (4H, complex, NHCO+N$^+$H$_2$+OH); 7.8—7.1 (9H, complex, aromatic H); 5.35 [1H, doublet (J=8 c/s), CHOH]; 4.48 (1H, complex, >N—CH—CO); 3.8—2.8 (complex, CH$_2$N); 2.4—1.7 (4H, complex, >NCH$_2$CH$_2$CH$_2$); 1.3 (6H, singlet, CH$_3$C);

(Example 9): 1-(2chlorophenyl-2-{2-[(N-phenylacetylprolyl)amino]-1,1-dimethyl-ethylamino}ethanol hydrobromide as a foam (44% yield), m.p.~78° C.; NMR (δ): 9.2—8.1 (4H, complex, NHCO+N$^+$H$_2$+OH); 7.8—7.1 (9H, complex, aromatic H); 5.3 [1H, doublet (J=8 c/s), CHOH); 4.3 (1H, complex >N—CH—CO); 3.8—2.8 (complex, CH$_2$N); 3.68 (singlet, PhCH$_2$CO); 2.2—1.6 (4H, complex, >NCH$_2$CH$_2$CH$_2$); 1.27 (6H, singlet, CH$_3$C);

(Example 10): 1-[3,4-bis(pivaloyloxy)phenyl]-2-{2-[(N-benzoyl-N-methyl-glycyl)amino]-1,1-dimethyl-ethylamino}ethanol hydrobromide as a foam (10% yield), m.p. 219°-220° C.; NMR (δ): 8.0—8.0 (3H, complex, NHCO+N$^+$H$_2$); 7.6—7.1 (8H, complex, aromatic H); 6.2 (1H, broad, CHOH); 4.93 (1H, broad, CHOH); 4.2+3.95 (2H, two singlets, NCH$_2$CO); 3.7—2.7 (complex, CH$_2$N+H$_2$O); 2.95 (3H, singlet, CH$_3$N); 1.3 (24H, singlet, CH$_3$C);

(Example 11): 1-(2-chlorophenyl)-2-{2-[(N-benzoyl-N-methylglycyl)amino]-1,1-dimethyl-ethylamino}ethanol hydrobromide as a foam (13% yield), m.p. ~132° C.; NMR (δ): 8.0−8.0 (3H, complex, NHCO+N$^+$H$_2$); 7.9−7.0 (9H, complex, aromatic H); 5.25 [1H, doublet (J=8 c/s), C$\underline{H}$OH]; 4.1+3.9 (2H, 2 singlets COC$\underline{H}_2$NCH$_3$); 4.0−2.7 (complex, CH$_2$N); 2.9 (3H, singlet, CH$_3$N); 1.3 (6H, singlet, CH$_3$C);

(Example 12): 1-[3,5-bis(pivaloyloxy)phenyl-2-{2-[(N-phenoxyacetylprolyl)amino]-1,1-dimethyl-ethylamino}ethanol hydrobromide as a foam (20% yield); NMR (δ): 8.7−8.1 (3H, complex, NHCO+N$^+$H$_2$); 7.4−6.7 (8H, complex, aromatic H); 6.3 (1H, broad, CHO$\underline{H}$); 4.95 (1H, broad, C$\underline{H}$OH); 4.78 (2H, singlet, PhOC$\underline{H}_2$CO); 4.32 (1H, complex, >N—CH—CO); 3.7−2.7 (complex, CH$_2$N+H$_2$O); 2.2−1.7 (4H, complex, >NCH$_2$C$\underline{H}_2$C$\underline{H}_2$);

(Example 13): 1-(3,4-bis(pivaloyloxy)phenyl-2-{2-[(N-phenoxyacetyl-N-methyl-glycyl)amino]-1,1-dimethylethylamino}ethanol hydrobromide, as a foam (8% yield), m.p. 100°−105° C.; NMR (δ): 8.8−8.0 (3H, complex, NHCO+N$^+$H$_2$); 7.5−6.7 (8H, complex, aromatic H); 6.2 (1H, singlet, CHO$\underline{H}$); 4.9−4.8 (3H, complex, C$\underline{H}$OH+PhOC$\underline{H}_2$CO); 4.15+4.02 (2H, 2 singlets, COC$\underline{H}_2$NCH$_3$); 3.6+2.7 (complex, CH$_2$N+H$_2$O); 3.1+2.87 (2 singlets, CH$_3$N); 1.35 (24H, singlet, CH$_3$C);

(Example 14): 1-[3,5-bis(pivaloyloxy)phenyl]-2-{2-[(N-benzoyl-piperidin-2-ylcarbonyl)amino]-1,1-dimethylethylamino}ethanol hydrobromide, as a foam (16% yield); NMR (δ): 8.0−8.0 (3H, complex, NHCO+N$^+$H$_2$); 7.7−6.8 (8H, complex, aromatic H); 5.0 [1H, doublet (J=8 c/s), CHOH]; 4.7−2.7 (complex, CO.CH.N<+CH$_{2i\ N+H_2O}$); 2.0−1.0 (6H, complex, >NCH$_2$C$\underline{H}_2$C$\underline{H}_2$CH$_2$); 1.33 (24H, singlet, CH$_3$C);

(Example 15): 1-[3,4-bis(pivaloyloxy)phenyl]-2-{2-[(N-benzoyl-piperidin-2-carbonyl)amino]-1,1-dimethylethylamino}ethanol hydrobromide, as a foam (5% yield); NMR (δ): 7.8−7.6 (3H, broad, NHCO+N$^+$H$_2$); 6.7−6.1 (8H, multiplet, aromatic); 5.3 (1H, broad singlet, CHO$\underline{H}$); 4.2−3.8 (2H, complex, C$\underline{H}$OH+>N—C$\underline{H}$—CO); 3.0−2.8 (complex, CH$_2$N+H$_2$O); 1.7−1.1 (30H, complex, CH$_3$C+>NCH$_2$C$\underline{H}_2$C$\underline{H}_2$CH$_2$);

(Example 16): 1-[3-(isobutyryloxymethyl)-4-(isobutyryloxy)phenyl]-2-{2-[(N-phenoxyacetyl-N-methyl-glycyl)amino]-1,1-dimethyl-ethylamino}ethanol hydrobromide, as a foam (16% yield); NMR (δ): 8.7−8.0 (3H, complex, NHCO+N$^+$H$_2$); 7.7−6.7 (8H, complex, aromatic H); 5.1−4.7 (5H, multiplet, CHOH+PhOCH$_2$); 4.18+4.04 (2H, 2 singlets, COCH$_2$); 3.8−2.6 (complex, CH$_2$N+H$_2$O); 3.08+2.86 (3H, 2 singlets, CH$_3$N); 1.3−1.05 (18H, multiplet, CH$_3$C);

(Example 17): 1-[3-(isobutyryloxymethyl)-4-(isobutyryloxy)phenyl]-2-{2-[(N-benzoyl-piperidin-2-carbonyl)amino]-1,1-dimethyl-ethylamino}ethanol hydrobromide as a viscous oil (6% yield); NMR (δ): 8.5−7.8 (3H, complex, NHCO+N$^+$H$_2$); 7.6−6.9 (8H, complex, aromatic H); 5.2−4.7 (complex, CH$_2$O+−C$\underline{H}$OH+H$_2$O); 4.5−1.4 (complex, CH$_2$N+>CHCO+>NCH$_2$C$\underline{H}_2$C$\underline{H}_2$CH$_2$); 1.25−1.10 (18H, 2 doublets+singlets, CH$_3$C);

(Example 18): 1-[3,4-bis(pivaloyloxy)phenyl]-2-{2-[(N-benzoyl-N-methyl-phenylalanyl)amino]-1,1-dimethyl-ethylamino}ethanol hydrobromide, as a foam (22% yield); NMR (δ): 8.9−8.1 (3H, complex, NHCO+N$^+$H$_2$); 7.6−6.7 (13H, complex, aromatic H); 4.96 [1H, doublet (J=8 c/s), C$\underline{H}$OH]; 4.55 (1H, triplet, CO.C$\underline{H}$.CH$_2$Ph); 3.47+3.38 (3H, 2 singlets, CH$_3$N); 3.6−2.6 (6H, complex, CH$_2$N, COCHC$\underline{H}_2$Ph); 1.28 (24H, singlet, CH$_3$C).

(Example 19): 1-[3,4-bis(pivaloyloxy)phenyl]-2-}2-[(N-phenoxyacetyl-N-methyl-β-alanyl)amino]-1,1-dimethylethylamino}ethanol hydrobromide, as a foam (8% yield): NMR (δ): 8.7−7.7 (3H, complex, NHCO+N$^+$H$_2$); 7.5−6.7 (12H, complex, aromatic H); 4.9-4.7 (3H, complex, C$\underline{H}$OH+PhOC$\underline{H}_2$); 3.9−2.7 (complex, CH$_2$N); 3.0+2.83 (2 singlets, CH$_3$N); 1.3 (24H, singlet, CH$_3$C);

(Example 20): 1-[3,4-bis(pivaloyloxy)phenyl]-2-{2-[(N-benzoyl-N-methyl-isoleucyl)amino]-1,1-dimethylethylamino}ethanol hydrobromide, as a foam (24% yield); NMR (δ): 9.3−8.1 (3H, complex, NHCO+N$^+$H$_2$); 7.7−7.0 (8H, complex, aromatic H); 5.0 [1H, doublet (J=8 c/s), C$\underline{H}$OH]; 4.5−2.7 (complex, CH$_2$N+—CO.CH.N<); 2.9 (singlet, CH$_3$N); 2.0 (complex, CH$_3$.C$\underline{H}$.Et); 1.35+1.2+0.9 [32H, 3 singlets, (CH$_3$)$_3$C—C$\underline{H}_3$.CH.E$\underline{t}$+(CH$_3$)$_2$C<];

(Example 21): 1-[3,4-bis(pivaloyloxy)phenyl]-2-{2-[(N-benzoyl-N-methyl-alanyl)amino]-1,1-dimethylethylamino}ethanol hydrobromide, as a solid (13% yield); m.p. ~200° C. (decomposition); NMR (δ): 8.9−8.1 (3H, complex, NHCO+N$^+$H$_2$); 7.6−7.0 (8H, complex, aromatic H); 3.7−3.0 (4H, complex, CH$_2$N); 2.9+2.88 (3H, 2 singlets, CH$_3$N); 1.45+1.30 (27H, 2 singlets, CH$_3$C);

(Example 22): 1-[3,4-bis(pivaloyloxy)phenyl]-2-{2-[(N-benzoyl-acetidin-2-carbonyl)amino]-1,1-dimethylethylamino}ethanol hydrobromide as a foam (10% yield), m.p. 130°−135° C.; NMR (δ): 8.8−8.0 (2H, complex, N$^+$H$_2$); 7.9 (1H, triplet, NHCO); 7.8−7.0 (8H, complex, aromatic H); 5.0 (2H, complex, C$\underline{H}$OH+—CO.CH.N<); 4.2 (2H, multiplet, NC$\underline{H}_2$CH$_2$CHCO); 3.8−2.8 (complex, C$\underline{H}_2$NH); 2.6−2.0 (complex, NCH$_2$C$\underline{H}_2$CHCO); 1.3 (24H, singlet, CH$_3$C);

(Example 23): 1-[3,4-bis(pivaloyloxy)phenyl]-2-{2-[(N-4-chlorobenzoyl-prolyl)amino]-1,1-dimethylethylamino}ethanol hydrobromide as a foam (10% yield), m.p. 120°−124° C.; NMR (δ): 8.4 (3H, complex, NHCO+N$^+$H$_2$); 7.7−7.1 (7H, complex, aromatic H); 4.85 [1H, doublet (J=8 c/s), C$\underline{H}$OH]; 4.40 (1H, singlet, >NCHCO); 3.9−2.8 (6H, complex, CH$_2$N—visible after treatment with d$_4$—AcOH); 2.2−1.6 (4H, complex, >NCH$_2$C$\underline{H}_2$C$\underline{H}_2$); 1.3 (24H, singlet, CH$_3$C);

(Example 24): 1-[4-(pivaloyloxy)phenyl]-2-{2-[(N-benzoyl-prolyl)amino]-1,1-dimethyl-ethylamino}ethanol hydrobromide as a solid (13% yield), m.p. 153°−158° C.; NMR (δ): 8.6−7.7 (3H, complex+triplet, NHCO+N$^+$H$_2$); 7.7−6.8 (9H, complex, aromatic H); 6.45 (1H, broad, CHO$\underline{H}$); 4.8 [1H, doublet, (J=8 c/s), C$\underline{H}$OH]; 4.4 (1H, complex >NCHCO); 3.8−2.7 (complex, CH$_2$N+H$_2$O); 2.3−1.7 (4H, complex, >NCH$_2$C$\underline{H}_2$C$\underline{H}_2$); 1.3 (15H, singlet, CH$_3$C);

(Example 25): 1-[3,4-bis(n-butyryloxy)phenyl]-2-{2-[(N-phenoxyacetyl-prolyl)amino]-1,1-dimethylethylamino}ethanol hydrobromide as a foam (5% yield), m.p. 93°−95° C.; NMR (δ): 8.7−8.0 (3H, complex, NHCO+N$^+$H$_2$); 7.4−6.6 (8H, complex, aromatic H); 6.15 (1H, broad, CHO$\underline{H}$); 4.85+4.70 [3H, doublet (J=8 c/s)+singlet, C$\underline{H}$OH+PhOC$\underline{H}_2$CO); 4.22 (1H, multiplet, >NCHCO); 3.9−2.7 (complex, CH$_2$N+H$_2$O); 2.45 (multiplet, COC$\underline{H}_2$CH$_2$CH$_3$); 2.2−1.7, 1.6 (8H, broad complex+multiplet, >NCH₂CH₂CH₂+CO CH₂CH₂CH₃); 1.22 (6H, singlet, CH₃C); 0.9 (6H, triplet, COCH₂CH₂CH₃);

(Example 26): 1-[3,4-bis(pivaloyloxy)phenyl]-2-{2-[(N-4-chlorophenylacetyl-prolyl)amino]-1,1-dimethylethylamino}ethanol hydrobromide, as a foam (14% yield), m.p. 109°-111° C.; NMR (δ): 8.7−8.0 (3H, complex, NHCO+N⁺H₂); 7.6−7.0 (7H, complex, aromatic H); 6.24 (1H, broad, CHOH); 4.88 [1H, doublet (J = 8 c/s), CHOH]; 4.26 (1H, multiplet, >NCHCO); 3.9−2.7, 3.68 (complex+singlet, PhCH₂CO+CH₂N+H₂O); 2.3−1.5 (4H, complex, >NCH₂CH₂CH₂); 1.3 (24H, singlet, CH₃C);

(Example 27): 1-[3,4-bis(pivaloyloxy)phenyl]-2-{2-[(N-benzoyl-N-n-butyl-glycyl)amino]-1,1-dimethylethylamino}ethanol hydrobromide, as a foam (18% yield), m.p. 175°-180° C. (decomposition); NMR (δ): 8.8−8.0 (3H, complex, NHCO+N⁺H₂); 7.7−7.0 (8H, complex, aromatic H); 4.95 (complex, CHOH+H₂O); 4.1, 3.95 (2H, 2 singlets, COCH₂N<); 3.7−2.7 (6H, complex, CH₂N); 2.0−1.0 (31H, complex+singlet, CH₃C+CH₃CH₂CH₂N);

(Example 28): 1-[3,4 -bis(pivaloyloxy)phenyl]-2-{2-[(N-t-butyloxycarbonyl-N-methyl-alanyl)amino]-1,1-dimethylethylamino}ethanol hydrobromide as a foam (10% yield); NMR (δ): 9.3−7.7 (3H, broad, CONH+N⁺H₂); 7.5−7.1 (3H, complex, aromatic H); 6.5−6.0 (1H, broad, CHOH); 5.1−4.8 (1H, broad doublet, CHOH); 4.7−4.3 (1H, broad quartet, COCHNCH₃); 4.2−2.9 (broad, CH₂N+H₂O); 2.8 (3H, singlet, NCH₃); 1.6−1.0 (36H, CH₃C+CH₃CH).

The necessary starting materials of formula V may be obtained using a similar procedure to that described in Example 1 for the production of N¹-(2-amino-2-methylpropyl)-N²-phenylacetyl-prolinamide, starting from the appropriate acid of formula VIII and 1,2-diamino-2-methylpropane:

(1) N¹-(2-amino-2-methylpropyl)-N²-benzoylpiperidin-2-carboxamide* (for Examples 6, 14, 15 and 17): isolated as an oil; NMR (CDCl₃)δ: 7.6−7.2 (5H, complex, aromatic H); 5.8−5.3 (1H, broad, NHCO); 3.6−2.8 (5H, complex, >NCHCO+CH₂N); 2.27 (2 H, singlet, NH₂); 2.0−1.0 (complex, NCH₂CH₂CH₂CH₂); 1.22+1.14 (6H, 2 singlets, CH₃C);

[*Note: throughout this specification compounds of formula V are named as derivatives of amides of amino acids i.e. N¹ refers to substituents on the amino nitrogen and N² refers to substituents on the amino nitrogen.

Thus, intermediate (1) is:

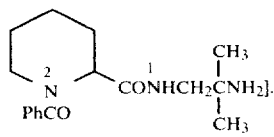

(2) N¹-(2-amino-2-methylpropyl)-N²-benzoylprolinamide (for Examples 7, 8 and 24): isolated as a foam; NMR (CDCl₃)δ: 7.6−7.2 (6H, complex, aromatic H+NHCO); 4.6+4.55 (3H, broad+singlet, >NCHCO+NH₂); 3.6−2.8 (4H, complex, CH₂N); 2.5−1.7 (4H, complex, NCH₂CH₂CH₂); 1.05 (6H, singlet, CH₃C);

(3) N¹-(2-amino-2-methylpropyl)-N²-benzoyl-N²-methylglycinamide (for Examples 10 and 11): isolated as an oil; NMR (CDCl₃)δ: 7.7−7.1 (6H, complex, aromatic H+NHCO); 4.1 (2H, singlet, NH₂); 3.3−3.0 (4H, complex, CH₂NH); 2.05 (3H, singlet, CH₃N); 1.05 (6H, singlet, CH₃C);

(4) N¹-(2-amino-2-methylpropyl)-N²-methyl-N²-phenoxyacetylglycinamide (for Example 16): isolated as an oil; NMR (CDCl₃)δ: 7.4−6.7 (6H, complex, aromatic H+NHCO); 4.73 (2H, complex, PhOCH₂); 4.0 (2H, singlet, NH₂); 3.2−2.8 (4H, complex, CH₂N); 2.35 (3H, singlet, CH₃N);

(5) N¹(2-amino-2-methylpropyl)-N²-benzoyl-N²-methylphenylalaninamide (for Example 18): isolated as a foam; NMR (CDCl₃)δ: 8.2+7.5 (1H, 2 triplets, NHCO); 7.6−6.9 (10H, complex, aromatic H); 5.4 (1H, broad, >NCHCO); 4.4 (2H, singlet, NH₂); 3.7−2.6 (7H, complex, PhCH₂+CH₂N+CH₃N); 1.2 (6H, singlet, CH₃C);

(6) N¹-(2-amino-2-methylpropyl)-N²-methyl-N²-phenoxyacetyl-β-alaninamide (for Example 19): isolated as an oil; NMR (CDCl₃)δ: 7.5−6.7 (6H, complex, aromatic H+NHCO); 4.8+4.63 (2H, singlets, PhOCH₂); 3.65 (2H, triplet, COCH₂CH₂N); 3.05 (5H, complex, CH₃N+C.CH₂N); 2.36 (2H, triplet, COCH₂CH₂N); 1.33 (2H, singlet, NH₂); 1.02 (6H, singlet, CH₃C);

(7) N¹-(2-amino-2-methylpropyl)-N²-benzoyl-N²-methylisoleucinamide (for Example 20): isolated as an oil; NMR (CDCl₃)δ: 7.7−7.0 (5H, complex, aromatic H); 5.9 (1H, broad, NHCO); 4.7+4.6 (2H, 2 singlets, >NCHCO); 3.4−2.7, +2.9 (7H, complex+singlet, CH₂NH+NH₂+CH₃N); 2.1 (complex, CH₃CHCH₂CH₃); 1.7−0.8 (14H, complex, CH₃.C+CH₃CHCH₂CH₃);

(8) N¹-(2-amino-2-methylpropyl)-N²-benzoyl-N-methyl alaninamide (for Example 21): isolated as an oil; NMR (CDCl₃)δ: 7.7−7.1 (6H, complex, aromatic H+NHCO); 5.2 (1H, broad, >NCHCO); 3.6−2.9+2.95 (5H, complex+singlet, CH₂NH+CH₃N); 1.55+1.4+1.2+1.1 [11H, singlet+doublet (J = 7 c/s)+doublet (J = 7 c/s)+singlet, NH₂+CHCH₃+CH₃C];

(9) N¹(2-amino-2-methylpropyl)-N²-benzoylazetidin-2-carboxamide (for Example 22): isolated as an oil; NMR (CDCl₃)δ: 8.0−7.3 (6H, complex, aromatic H+NHCO); 5.05 (1H, multiplet, >NCHCO); 4.23 (2H, multiplet, NCH₂CH₂); 3.2 (2H, multiplet, CH₂NH); 2.5 (2H, complex NCHCH₂CH₂); 1.45 (2H, singlet, NH₂); 1.1 (6H, singlet, CH₃C);

(10) N¹-(2-amino-2-methylpropyl)-N²-(4-chlorobenzoyl)prolinamide (for Example 23): isolated as an oil; NMR (CDCl₃)δ: 7.8−7.2 (5H, complex, aromatic H+NHCO); 4.7 (1H, broad, >NCHCO); 3.8−3.2 (4H, complex, CH₂N); 2.5−1.7+2.3 (6H, complex+singlet, NCH₂CH₂CH₂+NH₂); 1.15 (6H, singlet, CH₃C);

(11) N¹-(2-amino-2-methylpropyl)-N²-(4-chlorophenylacetyl)prolinamide (for Example 26): isolated as an oil; NMR (CDCl₃)δ: 7.7 (1H, triplet, NHCO); 7.4−7.0 (4H, complex, aromatic H); 4.4 (1H, complex >NCHCO); 3.9−2.8, +3.65+3.1 (8H, complex+2 singlets, CH₂N+PhCH₂CO+NH₂); 2.2−1.7 (4H, complex, NCH₂CH₂CH₂); 1.0 (6H, singlet, CH₃C);

(12) N¹-(2-amino-2-methylpropyl)-N²-benzoyl-N²-n-butylglycinamide (for Example 27): isolated as an oil; NMR (CDCl₃)δ: 7.7−7.4 (6H, complex, aromatic H+NHCO); 4.15 (2H, singlet, NCH₂CO); 3.7−3.1 (4H, complex NHCH₂+NCH₂CH₂CH₂CH₃); 1.93 (2H, singlet, NH₂); 1.9−0.8, +1.2+1.0 (13H, complex+2 singlets, CH₃C+NCH₂CH₂CH₂CH₃);

(13) N¹-(2-amino-2-methylpropyl)-N²-(t-butyoxycarbonyl)N²-methylalaninamide (for Example 28): isolated as a gum; NMR (CDCl₃)δ: 7.1−6.5 (1H, CONH); 5.0−4.3 (1H, multiplet, NCHCO); 3.3−3.0 (1H, multiplet, NHCH$_2$); 2.85 (3H, singlet, CH$_3$N); 2.1 (2H, singlet, NH$_2$); 1.7–1.0 (15H, complex, CH$_3$C).

The necessary acids of formula VIII were obtained as follows:

(a) by analogy with N-(phenylacetyl)proline in Example 1, but starting from the appropriate amino acid of formula X and acyl chloride of the formula Q.Cl, and had the following properties:

| Compound | m.p. (°C.) | Recrystallisation solvent |
|---|---|---|
| N-benzoylproline | 157–159 | EtOH |
| N-(4-chlorobenzoyl)proline | 130–132 | Toluene |
| N-benzoylazetidin-2-carboxylic acid | 112–114 | Toluene |
| N-benzoyl-N-methylglycine | 103–105 | Benzene |
| N-methyl-N-(phenoxyacetyl)glycine | 145–147 | EtOAc |
| N-benzoylpiperidin-2-carboxylic acid | 118–120 | Toluene/petrol* (60–80°) |

*Petroleum ether (b.p. 60–80° C.)

(b) as illustrated below for N-benzoyl-N-methylalanine:

Methyl iodide (140 ml.), followed by sodium hydride (40.32 g., 50% w/w dispersion in mineral oil), was added to a stirred solution of N-benzoyl-L-alanine (54.0 g.) in tetrahydrofuran (700 ml.) and dimethylformamide (70 ml.). The mixture was heated under reflux at 80° C. in a dry argon atmosphere for 24 hours, and then evaporated. Ether (50 ml.) was added to the residue and the mixture was evaporated to remove residual methyl iodide. The subsequent residue was partitioned between ethyl acetate (250 ml.) and water (250 ml.). The aqueous phase was extracted with ethyl acetate (2×250 ml.) and the combined organic phase were washed with water (250 ml.), then with saturated sodium chloride solution (250 ml.) and then dried (MgSO$_4$) and evaporated. The residue contained two clear immiscible oils.

The lower oil (N-benzoyl-N-methylalanine methyl ester) (40.0 g.) was separated and stirred for 16 hours with a mixture of aqueous sodium hydroxide (1 M, 800 ml.) and tetrahydrofuran (800 ml.). The tetrahydrofuran was then removed by evaporation. The aqueous residue was extracted with ether (2×250 ml.), cooled to 0° C. and acidified to pH2 with 4 M hydrochloric acid. The mixture was extracted with ethyl acetate (3×250 ml.). These extracts were combined, dried (MgSO$_4$) and evaporated to give N-benzoyl-N-methylalanine as a solid (38.0 g.) (m.p. 126°–127° C., after recrystallisation from water).

Using an analogous procedure, but starting from the appropriate amino acid of formula VIII (R$^5$=H) and methyl iodide or n-butyl iodide the following compounds were obtained:

| Compound | m.p. (°C.) | Recrystallisation solvent(s) |
|---|---|---|
| N-benzoyl-N-(methyl)phenylalanine | 137–140 | EtOAc |
| N-methyl-N-(phenoxyacetyl)-β-alanine | 121–123 | EtOAc/petrol (60–80°) |
| N-benzoyl-N-methylisoleucine | 112–114 | EtOAc/petrol (60–80°) |
| N-benzoyl-N-(n-butyl)glycine | 90–92 | Toluene |
| N-t-butyloxycarbonyl-N-methylalanine | 92–94 | Methylene chloride |

Certain of the amino acid starting materials of formula VIII (R$^5$=H) are not well known. They were obtained by acylation of the appropriate amino acid of formula X (R$^5$=H) and acyl chloride of the formula Q.Cl using a similar procedure to that described for N-phenylacetylproline in Example 1, and had the following properties:

| Compound | m.p. (°C.) |
|---|---|
| N-benzoylisoleucine | 117–119 (recrystallised from water) |
| N-(benzoyl)phenylalanine | 142–143 |
| N-(phenoxyacetyl)-β-alanine | 118–122 |
| N-benzoylalanine | 129–140 |

The additional glyoxal starting materials of formula IV were obtained in an analogous manner to 3,4-bis(pivaloyloxy)phenylglyoxal in Example 1 by dimethylsulphoxide oxidation of the appropriate 2-bromoacetophenone (itself obtained by bromination of the corresponding acetophenone) and had the following properties:

(1) 3,'4'-bis(n-butyryloxy)phenylglyoxal isolated as its oily hydrate; NMR (CDCl$_3$)δ: 8.0 (2H, multiplet, aromatic H); 7.3 (1H, multiplet, aromatic H); 6.27 (1H, broad, CHOH); 4.0−5.0 (2H, broad, CH$\underline{OH}$); 2.52 (4H, triplet, CO$\underline{CH_2}$CH$_2$CH$_3$); 1.76 (4H, sextet, COCH$_2$$\underline{CH_2}$CH$_3$); 1.02 (6H, triplet, COCH$_2$CH$_2$$\underline{CH_3}$);

(2) 4'-pivaloyloxyphenylglyoxal isolated as its oily hydrate; NMR (CDCl$_3$)δ: 8.15–7.2 (4H, multiplet, aromatic H); 7.5–6.5 (3H, broad, $\underline{CH}$OH); 1.36 (9H, singlet, CH$_3$C);

(3) 3',5'-bis(pivaloyloxy)phenylglyoxal isolated as its hydrate as a glass; NMR (CDCl$_3$)δ: 7.9–7.6 (2H, multiplet, aromatic H); 7.4−7.1 (1H, multiplet, aromatic H); 6.5; 5.8 (1H, complex, C$\underline{H}$OH); 5.2 (2H, broad singlet, CH$\underline{OH}$); 1.5 (18H, singlet, CH$_3$C);

(4) 2'-chlorophenylglyoxal isolated as its hydrate as a glass NMR (CDCl$_3$)δ: 7.8−7.1 (4H, complex, aromatic H); 6.2−5.85 (1H, multiplet, C$\underline{H}$OH); 3.8 (2H, broad singlet, CHO$\underline{H}$).

EXAMPLE 29

A suspension of 2-{N-benzyl-2[(N-phenylacetyl-prolyl)amino]ethylamino}-3',4'-bis(pivaloyloxy)acetophenone (4.6 g.) in 2-propanol (30 ml.) was cooled to −10° C. and sodium borohydride (0.68 g.) was added in two portions interspersed by a portion of methanol (12 ml.). After 2 hours at −10° C., a saturated aqueous solution (150 ml.) of sodium chloride was added and the mixture was extracted with ether (3×100 ml.). The combined ether extracts were washed with brine, dried (MgSO$_4$) and evaporated (4.5 g.). The residue 1-[3,4-bis(pivaloyloxy)phenyl]-2-{N-benzyl-2[(N-phenylacetyl-prolyl)amino]ethylamino}ethanol] was dissolved in ethanol (100 ml.) and the solution hydrogenated in the presence of 10% palladium on carbon (1.0 g.) at atmospheric pressure and room temperature during 3 hours. The catalyst was separated by filtration, washed with ethanol (10 ml.), and the filtrate and washings were evaporated. This residual oil was applied to the top of a column of silica gel (60 ART 9385, available from E Merck, Darmstadt, West Germany; 80 g.) and the column eluted with chloroform containing increasing amounts of methanol. The fractions eluted using a 4% v/v methanol-chloroform mixture were combined and evaporated. The residue was dissolved in chloroform and acidified with ethereal hydrogen bromide. Any excess acid was rapidly removed by evaporation with further chloroform. The residue was subjected to high vacuum until all traces of solvent were removed to give 1-[3,4-bis(pivaloyloxy)phenyl]-2-{2-[(N-phenylacetylprolyl)amino]ethylamino}ethanol hydrobromide as a foam (0.2 g.); NMR (δ): 8.7−8.2 (3H, complex NHCO and (N+H₂); 7.4−7.0 (9H, complex, aromatic H+OH); 4.9 (1H, broad C̲HOH); 4.25 (1H, multiplet, >NC̲HCO); 3.8−2.8 (10H, complex, CH₂N+PhCH₂); 2.2−1.7 (4H, complex, NCH₂C̲H₂C̲H₂); 1.25 (18H, singlet, CH₃C).

The necessary starting materials were obtained as follows:

(a) N-Benzyl-2-[(N-phenylacetyl-prolyl)amino]ethylamine

N-Phenylacetyl-proline (53.0 g.) was added in portions to a stirred solution of thionyl chloride (18.0 ml.) in methanol (96 ml.) maintained at −5° C. After the addition was complete, the reaction mixture was left at room temperature for 3 days and then evaporated. The residue was suspended in water (24 ml.), neutralised by addition of solid potassium carbonate, and extracted with ether (3×200 ml.). The extracts were washed with water (200 ml.), dried (MgSO₄) and evaporated to give N-phenylacetyl-proline methyl ester as a solid (51.1 g.) (m.p. 71°−72° C. after recrystallisation from cyclohexane).

A mixture of the methyl ester (49.1 g.) and 1,2-diaminoethane (35.76 g.) was heated at 95°–100° C. for 24 hours. Excess diamine was removed by evaporation and the residue was mixed with water. The mixture was separated by filtration and the aqueous phase evaporated. Remaining traces of water were removed by co-evaporation with toluene, to give 2-[(N-phenylacetyl-prolyl)amino]ethylamine as a solid (58.9 g.) which was used without further purification.

Benzaldehyde (22.3 g.) was added to a stirred solution of 2-[(N-phenylacetyl-prolyl)amino]ethylamine (57.8 g.) in ethanol (200 ml.). The mixture was stirred for 18 hours and then sodium borohydride (7.94 g.) was added in portions. The mixture was further stirred for 90 minutes and then the excess borohydride was destroyed by addition of acetic acid. The subsequent mixture was basified with 2 M sodium hydroxide solution and extracted with ethyl acetate (3×300 ml.). The combined extracts were washed with saturated sodium chloride solution (100 ml.) dried (MgSO₄) and filtered. The filtrate was carefully acidified with ethereal hydrogen bromide to give N-benzyl-2-[(N-phenylacetyl-prolyl)amino]ethylamine hydrobromide as a solide [58.9 g., after separation by decantation and washing with dry ether (2×200 ml.)].

The hydrobromide salt was suspended in water (200 ml.) and the suspension basified with solid potassium carbonate. The mixture was extracted with ethyl acetate (3×250 ml.). The combined extracts were dried (MgSO₄) and evaporated to give N-benzyl-2-[(N-phenylacetyl-prolyl)amino]ethylamine as an oil (26.3 g.); NMR (δ): 8.3−7.7 (1H, 2 triplets, NHCO); 7.5−6.9 (10H, complex, aromatic H); 4.45+4.19 (3H, multiplet+singlet, >NCHCO+PhC̲H₂NH); 3.8−2.6 (complex, NHCH₂CH₂N+PhC̲H₂CO); 2.2−1.5 (4H, complex, >NCH₂C̲H₂C̲H₂).

(b) 2-{N-Benzyl-2-[(N-phenylacetyl-prolyl)amino]ethylamino}-3′,4′-bis(pivaloyloxy)acetophenone hydrobromide A solution of 2-bromo-3′,4′-bis(pivaloyloxy)acetophenone (3.99 g.) and N-benzyl-2-[(N-phenylaceylprolyl)amino]ethylamine (7.3 g.) in dioxan (30 ml.) was stirred for 4 hours. The mixture was then diluted with dry ether (200 ml.), washed with water (3×100 ml.), then saturated sodium chloride solution (100 ml.), dried (MgSO₄) and filtered. The dry ethereal solution was then carefully acidified with ethereal hydrogen bromide and cooled to 0°-5° C. After 18 hours at that temperature the solid which had formed was separated by decantation to give 2-{N-benzyl-2-[(N-phenylacetylprolyl)amino]ethylamino}-3′,4′-bis(pivaloyloxy)acetophenone hydrobromide (4.7 g.) which was used without further purification.

[Note: it is to be understood that although in Examples 1–29 (where appropriate) the naturally occurring optically active amino acids L-proline, L-phenylalamine L-alaine and L-isoleucine were used as original starting materials, there is a possibility of some racemisation having occurred during the subsequent synthetic procedures. Consequently, the absolute configuration of the aminoacyl moiety in the final products of formula I has not been specified.]

EXAMPLE 30 (All parts by weight)

A mixture of finely divided 1-[3,5-bis(pivaloyloxy)-phenyl]-2-{2-[(N-phenoxyacetyl-prolyl)amino]-1,1-dimethyl-ethylamino}ethanol hydrobromide (0.5 parts) in propylene glycol (3.0 parts) and diethylene glycol monoethyl ether (2.0 parts) was added to a stirred mixture of lanolin (4.0 parts) and molten white soft paraffin (90.5 parts). The resulting mixture was allowed to cool to room temperature with rapid stirring until a uniform ointment containing 0.5% by weight of active ingredient suitable for topical administration to humans, was obtained.

The active ingredient may be replaced by another compound of formula I described hereinbefore preferably as its hydrochloride or hydrobromide salt.

EXAMPLE 31 (All parts by weight)

A solution of 1-[3,5-bis(pivaloyloxy)phenyl]-2-{2-[(N-phenoxyacetyl-prolyl)amino]-1,1-dimethyl-ethylamino}ethanol hydrobromide (1.0 parts) in ethanol (20 parts) and diethylene glycol monethyl ether (27 parts) was prepared. Purified water (50 parts) was added to the rapidly stirred solution, followed by carboxypolymethylene gelling agent (CARBOPOL* 940, available from B F Goodison Chemical Co., Cleveland, Ohio, USA; 2.0 parts). Stirring was continued until a finely dispersed gel, suitable for topical administration to humans was obtained.

[*CARBOPOL is a trade-mark].

The active ingredient may be replaced by another compound of formula I described hereinbefore, preferably as its hydrochloride or hydrobromide salt.

What is claimed is:

1. A 1-phenyl-2-aminoethanol derivative of the formula:

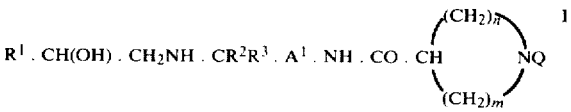

wherein R¹ is selected from the group consisting of 3,4-bis[(3−8C)alkanoyloxy]phenyl, 3,5-bis[(3−8C)alkanoyloxy]phenyl, 3-[(3−8C)alkanoyloxy]methyl-4-[(3−8C)alkanoyloxy]phenyl, 4-[(3−8C)alkanoyloxy]phenyl, 2-chlorophenyl and 3,5-dichloro-4-aminophenyl radicals; R² and R³ are independently hydrogen or (1−4−C)alkyl radicals; A¹ is a (1−4C)alkylene diradical; and Q is selected from the group consisting of (3–12C)alkanoyl, [(3–6C)alkoxy]carbonyl, phenylacetyl, phenoxyacetyl, benzoyl and benzyloxycarbonyl radicals, the phenyl rings of which may optionally bear a substituent selected from the group consisting of halogeno, (1–4C)alkyl, (1–4C)alkoxy and trifluoromethyl radicals [n is zero, 1 or 2; and m is 2,3,4 or 5,] and wherein the diradical of the formula:

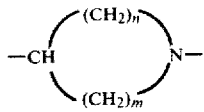   III is an azetidin-1,2-diyl, pyrrolidin-1,2-diyl, pyrrolidin-1,3-diyl, piperidin-1,2-diyl, piperidin-1,3-diyl or piperidin-1,4-diyl radical; or a pharmaceutically acceptable acid-addition salt thereof.

2. A compound as claimed in claim 1 wherein in $R^1$ the (3–8C)alkanoyloxy radical is selected from the group consisting of 2,2-dimethylpropionyloxy, isobutyryloxy, n-butyryloxy, n-pentanoyloxy and 3,3-dimethylbutyryloxy radicals; $R^2$ and $R^3$ are independently hydrogen or methyl radicals; $A^1$ is a methylene or ethylene diradical; and Q is selected from the group consisting of isobutyryl, dodecanoyl, t-butoxycarbonyl and phenylacetyl, phenoxyacetyl, benzoyl and benzyloxycarbonyl radicals, the phenyl rings of which may optionally bear a substituent selected from the group consisting of fluoro, chloro, bromo, methyl, methoxy and trifluoromethyl radicals.

3. A compound as claimed in claim 1 wherein $R^1$ is selected from the group consisting of 3,4-bis(pivaloyloxy)phenyl, 3,5-bis(pivaloyloxy)phenyl, 3,4-bis(butyryloxy)phenyl, 3-(isobutyryloxymethyl)-4-(isobutyryloxy)phenyl, 4-(pivaloyloxy)phenyl, 2-chlorophenyl and 3,5-dichloro-4-aminophenyl radicals; $R^2$ and $R^3$ are both hydrogen or methyl radicals; $A^1$ is a methylene diradical; and Q is selected from the group consisting of t-butoxycarbonyl, benzyloxycarbonyl, phenylacetyl, phenoxyacetyl, benzoyl, 4-chlorophenylacetyl and 4-chlorobenzoyl radicals.

4. An acid-addition salt as claimed in claim 1 which is a salt with an acid selected from the group consisting of hydrochloric, hydrobromic, phosphoric, sulphuric, oxalic, tartaric, lactic, fumaric, citric, acetic, salicylic, benzoic, β-naphthoic, methanesulphonic and adipic acid.

5. A compound as claimed in claim 1 wherein the diradical of the formula III is an azetidin-1,2-diyl, pyrrolidin-1,2-diyl or piperidin-,2-diyl radical.

6. A pharmaceutical composition for use in the topical treatment of inflammation affecting the skin of a warm-blooded animal comprising an effective amount of a compound of the formula I as claimed in claim 1, or a pharmaceutically acceptable acid-addition salt thereof, in association with a pharmaceutically acceptable excipient in a form suitable for topical administration.

7. A method for treating an area of inflammation affecting the skin of a warm-blooded animal which comprises topically administering to said area an effective anti-inflammatory amount of a compound of formula I, or a pharmaceutically acceptable acid-additon salt thereof, as claimed in claim 1.

8. A compound selected from the group consisting of 1-[3,4-bis(pivaloyloxy)phenyl]-2-{2-[(N-phenylacetyl-prolyl)amino]-1,1-dimethyl-ethylamino}ethanol; 1-(2-chlorophenyl)-2-{2-[(N-benzoyl-piperidin-2-carbonyl)amino]-1,1-dimethyl-ethylamino}ethanol; 1-[3,5-bis(pivaloyloxy)phenyl]-2-{2-[(N-phenoxyacetyl-prolyl)amino]-1,1-dimethyl-ethylamino{ethanol 9. 1-(2-Chlorophenyl)-2-{2-[(N-benzoylpiperidin-2-carbonyl)-amino]-1,1-dimethyl-ethylamino}ethanol; or a pharmaceutically acceptable acid-addition salt thereof.

* * * * *